(12) United States Patent
Partain (10) Patent No.: US 9,545,526 B1
(45) Date of Patent: Jan. 17, 2017

(54) SYSTEM AND METHOD FOR PROJECTION IMAGE TRACKING OF TUMORS DURING RADIOTHERAPY

(71) Applicant: Larry D. Partain, Los Altos, CA (US)

(72) Inventor: Larry D. Partain, Los Altos, CA (US)

( * ) Notice: Subject to any disclaimer, the term of this patent is extended or adjusted under 35 U.S.C. 154(b) by 141 days.

(21) Appl. No.: 14/484,142

(22) Filed: Sep. 11, 2014

(51) Int. Cl.
*A61N 5/10* (2006.01)

(52) U.S. Cl.
CPC ............. *A61N 5/1067* (2013.01); *A61N 5/10* (2013.01); *A61N 5/1048* (2013.01); *A61N 5/1049* (2013.01); *A61N 5/1064* (2013.01); *A61N 5/1065* (2013.01); *A61N 5/1071* (2013.01); *A61N 2005/1054* (2013.01); *A61N 2005/1074* (2013.01)

(58) Field of Classification Search
CPC ...... A61N 5/10; A61N 5/1048; A61N 5/1049; A61N 2005/1054; A61N 5/1064; A61N 5/1065; A61N 5/1067; A61N 5/1071
USPC ............................... 378/65, 98.8; 250/370.09
See application file for complete search history.

(56) References Cited

U.S. PATENT DOCUMENTS

| | | | | |
|---|---|---|---|---|
| 5,138,167 A | * | 8/1992 | Barnes | G01T 1/202 250/363.02 |
| 5,619,042 A | * | 4/1997 | Hughes | A61N 5/10 250/252.1 |
| 5,754,622 A | * | 5/1998 | Hughes | G21K 1/04 378/108 |
| 6,097,787 A | * | 8/2000 | Siochi | A61N 5/1031 378/62 |
| 6,208,712 B1 | * | 3/2001 | Hernandez-Guerra | A61N 5/1048 250/492.1 |
| 6,260,999 B1 | * | 7/2001 | Wofford | A61N 5/1049 378/163 |
| 6,272,207 B1 | * | 8/2001 | Tang | G21K 1/025 378/149 |
| 6,353,655 B1 | * | 3/2002 | Siochi | A61N 5/1031 378/62 |

(Continued)

OTHER PUBLICATIONS

A. Richter et al., Feasibility Study for Markerless Tracking of Lung Tumors in Stereotactic Body Radiotherapy, International Journal of Radiation Oncology, Biology, and Physics, vol. 78, No. 2, 2010, pp. 618-627.

(Continued)

*Primary Examiner* — Allen C. Ho
(74) *Attorney, Agent, or Firm* — William Nuttle (57) ABSTRACT

A system and method are provided for imaging and treatment of tumorous tissue in a patient. In an embodiment, the system includes a radiation source for generating a radiation beam comprising high-energy photons with low energy distributions for high contrast imaging along with high energy distributions for efficient treatment dose delivery. The radiation source includes a charged particle accelerator that generates charged particles having energies of less than 6 megavolts (MV), a target to receive the charged particles and generate the high-energy photons of the radiation beam, and a collimator to emit the radiation beam. The system further includes an imaging device of high detective quantum efficiency to define a target region of the tumorous tissue in the patient using the radiation beam, and a controller to determine the shape and modulate the dose for treatment of the tumorous tissue based on the defined target region, using the radiation beam.

9 Claims, 5 Drawing Sheets

(56) References Cited

U.S. PATENT DOCUMENTS

| | | | | |
|---|---|---|---|---|
| 6,366,641 B1 * | 4/2002 | Whitham | | H05H 9/04 250/492.3 |
| 6,445,766 B1 * | 9/2002 | Whitham | | A61B 6/00 378/124 |
| 6,459,762 B1 * | 10/2002 | Wong | | A61N 5/10 378/65 |
| 6,465,957 B1 * | 10/2002 | Whitham | | H05H 9/04 378/65 |
| 6,477,229 B1 * | 11/2002 | Grosser | | A61N 5/1031 378/65 |
| 6,487,274 B2 * | 11/2002 | Bertsche | | A61N 5/10 378/124 |
| 6,493,424 B2 * | 12/2002 | Whitham | | H05H 9/04 378/137 |
| 6,519,316 B1 * | 2/2003 | Collins | | A61N 5/1049 378/65 |
| 6,535,574 B1 * | 3/2003 | Collins | | A61N 5/1049 378/20 |
| 6,727,503 B1 * | 4/2004 | Gerstenmayer | | G01T 1/24 250/367 |
| 6,842,502 B2 * | 1/2005 | Jaffray | | A61B 6/032 378/19 |
| 6,878,944 B1 * | 4/2005 | Gerstenmayer | | G01T 1/2935 250/374 |
| 7,030,386 B2 * | 4/2006 | Pang | | G01T 1/2935 250/370.09 |
| 7,085,347 B2 * | 8/2006 | Mihara | | A61N 5/10 378/197 |
| 7,188,999 B2 * | 3/2007 | Mihara | | A61N 5/10 378/17 |
| 7,239,684 B2 * | 7/2007 | Hara | | A61N 5/1049 378/65 |
| 7,397,044 B2 * | 7/2008 | Calderon | | A61N 5/1048 250/370.08 |
| 7,668,292 B1 * | 2/2010 | Bose | | A61N 5/1049 378/65 |
| 7,671,342 B2 * | 3/2010 | Bani-Hashemi | | G01T 1/2008 250/370.09 |
| 7,804,936 B2 * | 9/2010 | Pouliot | | A61B 6/466 378/65 |
| 7,884,438 B2 | 2/2011 | Partain et al. | | |
| 7,945,021 B2 * | 5/2011 | Shapiro | | A61B 6/032 378/19 |
| 8,284,898 B2 * | 10/2012 | Ho | | H05H 7/12 315/505 |
| 8,355,482 B2 * | 1/2013 | Brown | | A61N 5/1049 378/124 |
| 8,440,978 B2 * | 5/2013 | Morf | | G01T 1/2018 250/370.09 |
| 8,483,803 B2 | 7/2013 | Partain et al. | | |
| 8,565,377 B2 * | 10/2013 | Robar | | A61N 5/1049 378/62 |
| 8,633,445 B2 * | 1/2014 | Star-Lack | | A61B 6/032 250/363.02 |
| 8,658,960 B2 | 2/2014 | Partain et al. | | |
| 8,774,351 B2 * | 7/2014 | Funk | | A61B 6/4488 378/62 |
| 2006/0262898 A1 | 11/2006 | Partain et al. | | |

OTHER PUBLICATIONS

J. Seppi et al., Megavoltage Cone-Beam Computed Tomography Using a High-Efficiency Image Receptor, International Journal of Radiation Oncology, Biology, and Physics, vol. 55, No. 3, 2003, pp. 793-803.

J. Rottmann et al.,Real-time soft tissue motion estimation for lung tumors during radiotherapy delivery, International Journal of Medical Physics Research and Practice, vol. 40, No. 9, Sep. 2013, pp. 1-7.

J. Robara et al., Megavoltage Planar and Cone-Beam Imaging With Low-Z Targets: Dependence of Image Quality Improvement on Beam Energy and Patient Separation, International Journal of Medical Physics Research and Practice, vol. 36, No. 9, Sep. 2009, pp. 3955-3963.

D. Roberts, et al., Comparative Study of a Low-Z Cone-Beam Computed Tomography System, Institute of Physics and Engineering in Medicine, vol. 56, 2011, pp. 4453-4464.

* cited by examiner

SYSTEM AND METHOD FOR PROJECTION IMAGE TRACKING OF TUMORS DURING RADIOTHERAPY

TECHNICAL FIELD

The present disclosure relates generally to a system and method of providing radiation imaging and/or treatment, and more particularly to systems and methods for tracking of tumors during for projection image tracking of tumors during radiotherapy.

BACKGROUND

A Radiation therapy is widely used to identify and treat tumors in a patient. In radiation therapy, a high energy collimated beam of ionizing radiation is used to target tumorous tissue in the patient. The ionizing radiation damages the DNA of tissue in the tumor leading to cellular death and destroying the tumor. It will be understood that both the dose and placement of the ionizing radiation must be accurately controlled to ensure that the tumor receives sufficient radiation to destroy tumor tissue while damage to the surrounding healthy tissue is minimized. This can be problematic as in many therapies using conventional radiation therapy systems, since the patient's anatomy will often shift or move during the treatment, for example breathing induced movement. This movement can significantly reduce the accuracy and effectiveness of the radiotherapy treatment, particularly for therapies such as hypofractionated stereotactic body radiotherapy (SBRT) in which a highly collimated beam is used to deliver a high biological dose of radiation directly to the tumor.

Generally, there are two approaches for ensuring that the tumor receives sufficient radiation to destroy tumor tissue while damage to the surrounding healthy tissue is minimized. The first uses radiation-absorbing internal or external markers on the object (e.g., patient) on an initial or set-up scan, which a radiation therapist can use set the collimated beam of ionizing radiation relative to the markers. While useful for initial set-up, this approach has little utility in maintaining the collimated beam on the targeted tumor when the tumor moves unseen inside the patient.

A second approach uses megavoltage (MV) computed tomography (CT) imaging device. In this approach, the imaging device, commonly referred to as an MV electronic portal imaging device (EPID), is incorporated within the therapeutic radiation system, providing a beams-eye-view (BEV) of the tumor and the area being irradiated. This approach is attractive because it can be used to generate images of the tumor and surrounding soft-tissue immediately before, during or immediately following administration of a therapeutic dose of ionizing radiation. Moreover, an MV EPID can typically be implemented or retrofitted to a therapeutic radiation system without major changes to a linear accelerator of system used to generate the collimated beam of ionizing radiation.

In principle, an MV EPID can generate high contrast images of a tumor and surrounding soft-tissue contrast without the use of markers. However, in practice prior art EPID images exhibit low contrast. In one study, detailed in A. Richter et al., Feasibility Study for Markerless Tracking of Lung Tumors in Stereotactic Body Radiotherapy, International Journal of Radiation Oncology, Biology, and Physics, Vol. 78, no. 2, 2010, pp. 618-627, the EPID images were only clear enough to track less than about 47% of the tumors of the 40 patients in their study.

Hence there is a need for an improved system and method for projection image tracking of tumors during radiotherapy.

SUMMARY

A system and method are provided for imaging and treatment of tumorous tissue in a patient.

In a first aspect, the invention is directed to a system including a radiation source for generating a radiation beam comprising high-energy photons for both high contrast imaging with lower photon energy distributions and efficient treatment of tumorous tissue with higher photon energy distributions, in a patient. The radiation source includes a charged particle accelerator that generates charged particles having energies of less than 6 megavolts (MV), a target of low Z to receive the charged particles and generate the high-energy photons of the radiation beam, and a collimator to emit the radiation beam. The system further includes an imaging device of high detective quantum efficiency (DQE) to define a target region of the tumorous tissue in the patient using the radiation beam, and a controller to determine a location and modulate the dose distribution for treatment of the tumorous tissue based on the defined target region, and to control the collimator to deliver radiation to the target region using the radiation beam.

In another aspect, the invention is directed to a method of treating a patient using such a system. Generally, the method includes: generating charged particles having energies of less than 6 megavolts (MV); applying the charged particles to a target of low $Z<74$ to generate a radiation beam comprising high-energy photons emitted by the target; defining a target region of tumorous tissue in the patient using the radiation beam and an imaging device with a high $DQE(0)>0.04$; determining a location and dose for treatment of the tumorous tissue based on the defined target region; and controlling the radiation beam to deliver radiation to the target region.

BRIEF DESCRIPTION OF THE DRAWINGS

Embodiments of the present invention will be understood more fully from the detailed description that follows and from the accompanying drawings and the appended claims provided below, where:

DETAILED DESCRIPTION

The present disclosure is directed generally to projection image tracking of tumors during radiotherapy, and more particularly to a system and method for imaging and treatment of tumorous tissue in a patient.

The best cancer treatment delivery is obtained at MV (megavoltage) energies. It is possible to also image at MV energies and this can provide a tremendous targeting advantage because one can simultaneously see where the treatment dose is being delivered while the treatment process is in progress. The great advantage this gives is the opportunity to modulate in real time, the shape and dose distribution (across the shape) for maximum treatment dose delivery effectiveness to the cancer lesion while sparing surrounding healthy tissue from the strongly damaging effects of the radiation. This surrounding dose damage issue is a major and poorly solved problem currently in the field of radiation therapy.

Disclosed herein is a system and method that combines a reduction in MV energy of the treatment beam (e.g. from 4 to 6 MV), a lowering of the atomic number (Z) of a target material from that of the typically used tungsten (Z=74) to a material with a substantially lower Z, and use of an imager having a high detective quantum efficiency (DQE). In particular it is noted that the reduction in MV energy and lowering of the atomic number (Z) provide a larger fraction of the X-ray photons with energies down in the kV range, which provides better image contrast while still maintaining enough MV photons for good treatment delivery.

In the following description, numerous specific details are set forth, such as specific configurations, compositions, and processes, etc., in order to provide a thorough understanding of the present invention. In other instances, well-known systems and methods in the field of radiotherapy have not been described in particular detail in order to not unnecessarily obscure the present invention. Furthermore, it is to be understood that the various embodiments shown in the Figures are illustrative representations and are not necessarily drawn to scale.

An embodiment of a therapeutic radiation system including a megavoltage (MV) electron beam target, a computed tomography (CT) electronic portal imaging device (EPID), and method of using the same to and treat tumorous tissue in a patient will now be described in detail with reference to FIGS. 1 through 7.

Figure 1:
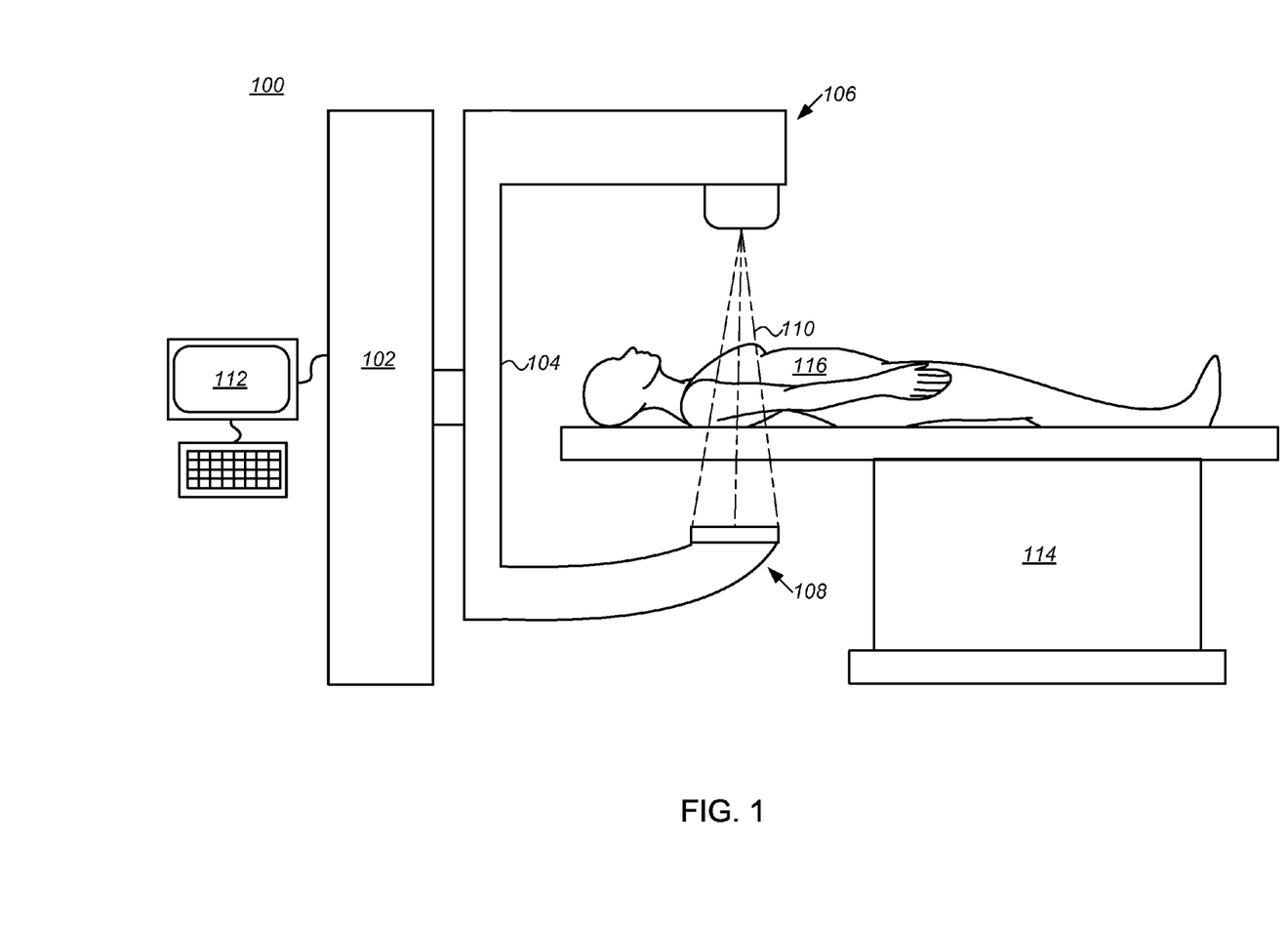
FIG. 1 is a block diagram of a radiation system with a low Z target for megavoltage (MV) imaging and treatment of tumorous tissue in a patient according to an embodiment of the present invention.

FIG. 1 is a block diagram of a radiation system including an MV imaging device according to some embodiments. Referring to FIG. 1, the radiation system 100 includes a controller 102, a gantry 104 rotatably attached to the controller 102, and a radiation source 106 and imaging device 108 at distal ends of the gantry 104 in facing opposition to one another such at a beam or cone of radiation 110 emitted by the radiation source 106 impinges on or is received by the imaging device 108. Generally, as in the embodiment shown the radiation system 100 further includes operator terminal 112 to enable an operator to operate the radiation system 100 and a couch 114 on which the patient 116 is positioned during imaging and/or treatment. Couch 114 is adjustable to enable, along with rotation of gantry 104, the rotation of radiation source 106 and imaging device 108 around a predetermined isocenter, such as a targeted tumor, before, during and after emission of radiation 110 for therapeutic or imaging purposes. The operator terminal 112 is typically located apart from the remainder of the radiation system 100, such as in a heavily shielded enclosure or separate room, in order to protect the operator from unnecessary exposure to radiation.

Figure 2:
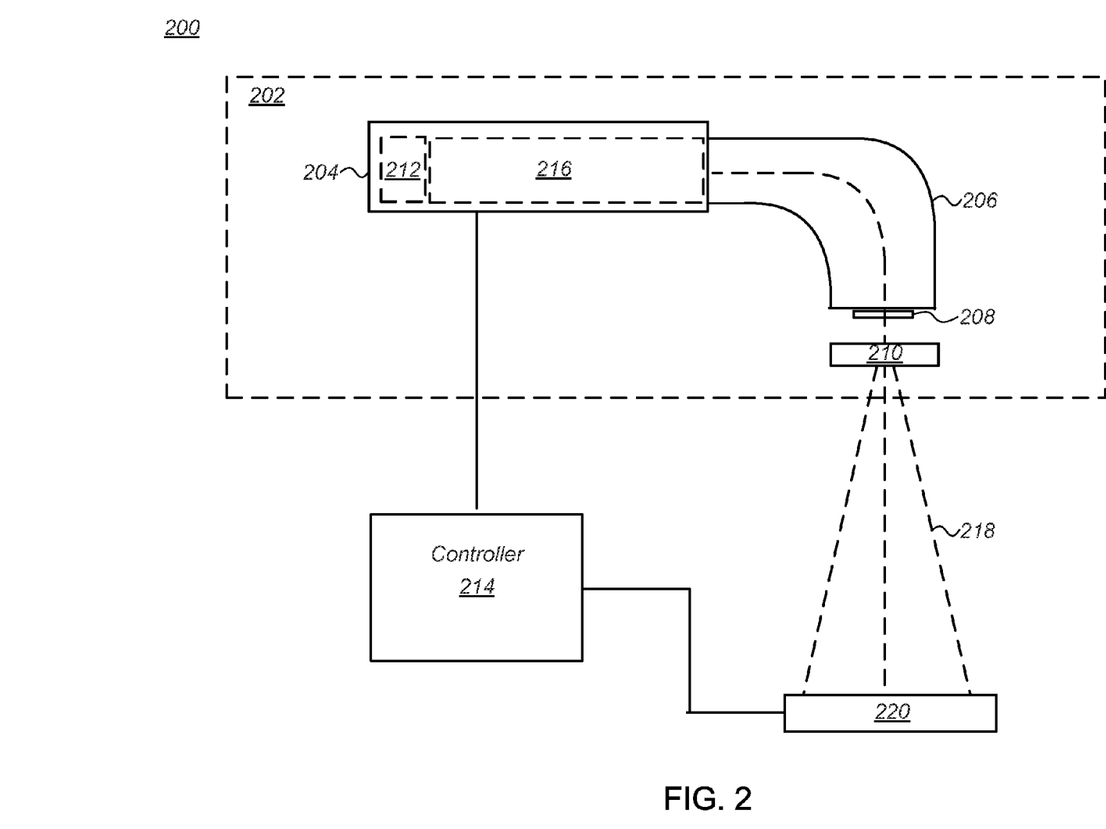
FIG. 2 is a block diagram of a radiation source for generating a therapeutic radiation beam for both imaging and treatment of tumorous tissue in a patient

A radiation source for generating a therapeutic radiation beam for both imaging and treatment of tumorous tissue in a patient will now be described in detail with reference to FIG. 2. FIG. 2 is a block diagram of a portion of a radiation system 200 including a radiation source 202, a controller 214 and at least a portion of an MV imaging device 220 according to some embodiments. It is noted that well-known systems in the field of radiotherapy have not been described in detail in order to not unnecessarily obscure the present invention. Furthermore, it is to be understood that the various features of the embodiment shown in FIG. 2 are illustrative representations and are not necessarily drawn to scale.

Referring to FIG. 2, the radiation source 202, includes a linear accelerator 204, a curved charged particle trajectory enclosure 206, an x-ray target or target 208 for generating X-rays and a collimator 210. The linear accelerator 204 includes a charged-particle source 212, such as an electron gun, powered and controlled by a controller 214 for injecting charged-particles such as electrons into an accelerator waveguide 216. The accelerator waveguide 216 is designed and fabricated so that electric fields accelerate the charged-particles. The curved enclosure 206 is positioned adjacent to an electromagnet such that charged-particles of a desired energy are selected by varying the strength of a magnetic field to which the curved enclosure 206 is exposed. The x-ray target 208 generates x-rays when struck by charged-particles of a desired energy. X-rays generated or emitted by the x-ray target 208 are then focused or collimated by the collimator 210. The collimator 210 generally includes one or more collimator plates as are known in the art to focus or collimate the x-rays into a patterned and modulated cone of x-ray radiation 218 that is passed through a patient (not shown in this figure) and impinges on an imager 220 of the imaging device that generates image signal/data in response to radiation incident thereon. The collimator 210 is then operated or controlled by the controller 214 to focus or collimate the x-rays into a narrower cone or beam of x-ray radiation (not shown in this figure) to deliver radiation to substantially just a target region in the patient. Optionally, the controller 214 can further receive a current or voltage signal from the imager 220 proportional to the radiation dose delivered to the target region using the radiation beam to monitor and control the dose.

In accordance with embodiments of the present invention the x-ray target 208 is or includes a material having a low atomic number (Z). By a low atomic number it is a meant a material having a Z number less than that of Tungsten, Z=74, which is commonly used in such applications. The use of an x-ray target 208 having a lower Z number provides higher contrast than conventional MV electronic portal imaging devices (EPID) which allows better beams-eye-view (BEV) tracking of tumor motion during stereotactic body radiotherapy (SBRT). Lowering Z increase the distribution of lower energy photons that provide high contrast while still maintaining a good distribution of higher energy photons needed for efficient treatment dose delivery. Moreover, the higher contrast enables superior tracking.

In one embodiment, the x-ray target 208 is or includes a metal, such as an Aluminum plate (Z=13) having a thickness of between about 0.1 and about 10 cm, and more preferably a thickness of between about 0.3 and about 3 cm. In another embodiment, the x-ray target 208 is or includes a Beryllium plate (Z=4) having a thickness of between about 0.1 and about 10 cm.

In another embodiment, the x-ray target 208 is or includes a non-metal material having a having a low atomic number (Z). For example, in one embodiment the x-ray target 208 is or includes a carbon plate (Z=12) having a thickness of between about 0.4 and about 6 cm.

Figure 3:
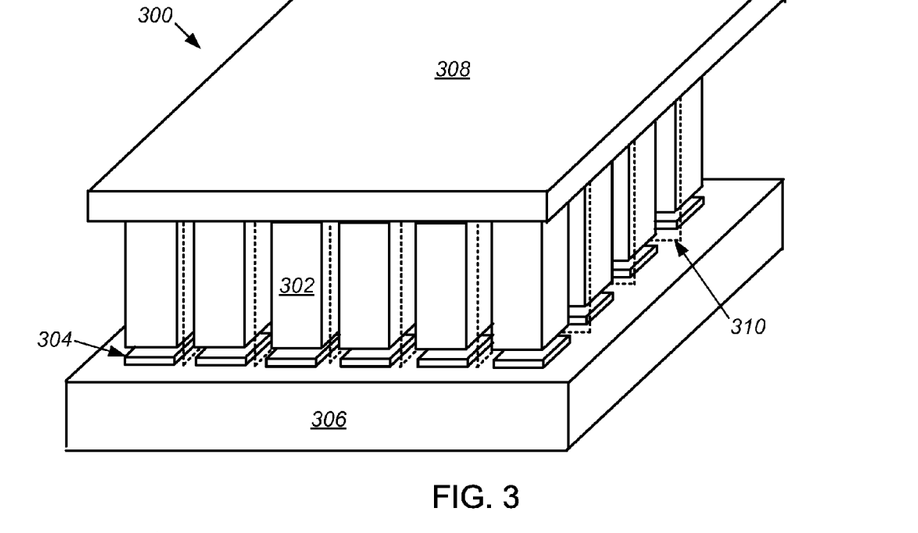
FIG. 3 is a block diagram of a high detective quantum efficiency (DQE) flat panel imager for use with the system and method of the present invention.

As discussed previously, the imaging device includes an imager that generates image signal/data in response to radiation incident thereon. Referring to FIG. 3, in one embodiment the imager 300 includes a scintillator layer 302 that includes a scintillator element, such as Cesium Iodide (CsI), an array of photo-detectors 304, such as photo-diodes with thin film transistors (TFT) switches, formed on a substrate 306 and a thin metal layer 308 overlying the scintillator layer 302. The scintillator layer 302 generates light photons in response to x-ray radiation, and the array of photo-detectors 304 generates an electrical signal in response to the light photons from the scintillator layer 302. The thin metal layer 308 can include, for example, aluminum or copper, and serves to protect and block ambient light from the scintillator layer 302. In the illustrated embodiment, the scintillator element of the scintillator layers 302 is separated by a number of optically opaque dividers 310 into a number of cells dimensionally matched to the pixels of the underlying array of photo-detectors 304, such that incoming light photons within a cell are accurately registered to the appropriate pixel within the array of photo-detectors 304.

Figure 4:
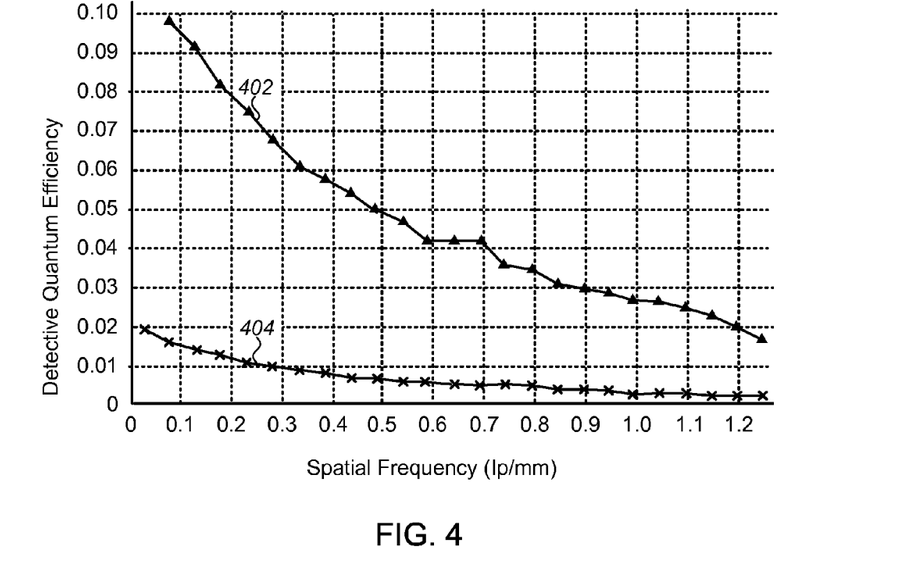
FIG. 4 is a graph illustrating the high DQE of the imager of FIG. 3 as compared to a conventional imager.

FIG. 4 is a graph illustrating the detective quantum efficiency (DQE) of the imager of FIG. 3 as compared to a conventional imager 300. DQE describes the effective number of Poisson-distributed x-ray quanta contributing to image signal to noise ratio and can be defined as the ratio of the signal-to-noise output image (squared) divided by the signal-to-noise input (squared) of the incident X-ray photon image. In a perfect imager, there would be no reduction in signal-to-noise and this ratio (DQE) would equal 1.0. FIG. 4 graphs the DQE of the imager 300 of FIG. 3 (line labeled 402) and a conventional imager (line labeled 404), relative to spatial frequency of the x-rays incident on the imager expressed squared-signal-to-noise-ratios per mm (lp/mm). Referring to FIG. 4 it is seen that the imager 300 of FIG. 3 has a high DQE at least 5 to as much as 10 times greater than for a conventional imager. By high DQE it is meant a DQE at zero spatial frequency (DQE(0)) of greater than 0.04, i.e., DQE(0)>0.04. In contrast the low DQE value for the conventional imager results in poor or low contrast images of the tumorous tissue making targeting of the tumor problematic, and can result in too high a dose being delivered to the patient when the system is operated in therapeutic mode and a signal from the imager is used to monitor dose.

Figure 5:
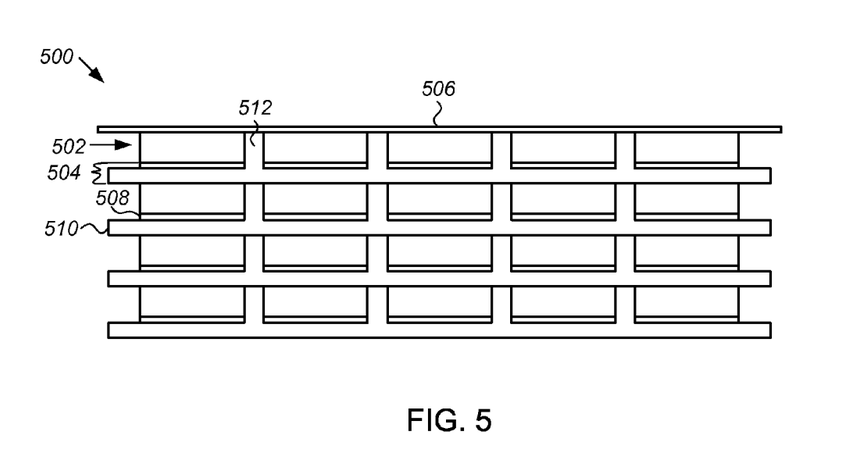
FIG. 5 is a block diagram of a high DQE flat panel imager including multiple, alternating scintillator and photo-detector layers for use with the system and method of the present invention.

Referring to FIG. 5, in an alternative embodiment the imager can include multiple, pixilated, alternating scintillator and photo-detector layers. In the embodiment shown in FIG. 5, the imager 500 includes 4 alternating or interleaved scintillator layers 502 and photo-detector layers 504 underlying or overlaid by a thin, metal layer 506. The thin metal layer 506 can include a layer of aluminum or copper, and serves as a buildup plate that absorbs more X-ray photon than non-metals but is thin enough to create photoelectrons that can be transmitted to and absorbed in the underlying scintillator layer 502 to increase detected signal levels, while also blocking external light that would otherwise add to noise. Each scintillator layer 502 can include an about 0.8 mm thick layer of an x-ray conversion material, such as Lanex®, commercially available from Kodak Corporation of Rochester, N.Y. Each photo-detector layer 504 includes an array of photo-detectors 508, such as light sensitive photo-diodes with light sensitive thin film transistors (TFT), formed on a substrate 510. The phosphor or x-ray conversion material, such as Lanex®, of the scintillator layers 502 is separated by a number of optically opaque dividers 512 into a number of cells dimensionally matched to the pixels of the underlying array of photo-detectors 508, such that incoming photons within a cell are accurately registered to the appropriate pixel within the array of photo-detectors 508. Optionally, in an embodiment not shown, the imager 500 can further include a light filter between each scintillator layer 502 and photo-detector layer 504 to reduce scintillator emitted light, thereby avoiding saturation of the photo-detector array. Suitable light filters reduce the light by factor a factor of from about 2× to about 100λ.

Figure 6:
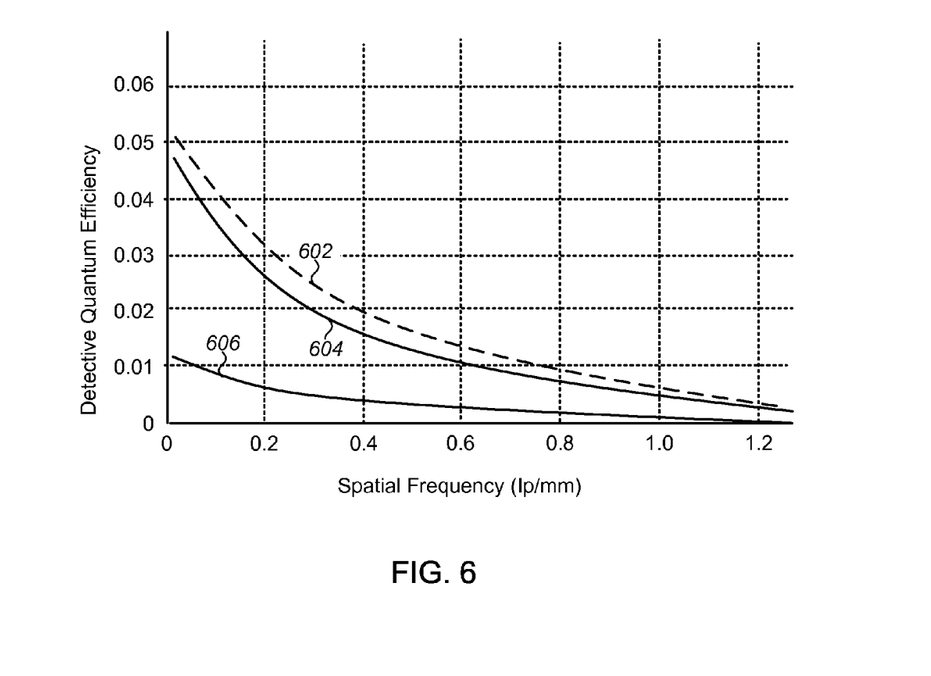
FIG. 6 is a graph illustrating the high DQE of the portal imager of FIG. 5 as compared to a conventional single layer imager.

FIG. 6 is a graph illustrating the DQE of the imager 500 of FIG. 5 as compared to a theoretical maximum DQE for an imager including multiple, alternating scintillator and photo-detector layers, and a conventional single layer imager. Referring to FIG. 6 the dashed line labeled 602 indicates the theoretical maximum DQE. The line labeled 604 indicates an actual measured DQE for imager 500 including four alternating scintillator layers 502 and photo-detector layers 504. The line labeled 606 indicates an actual measured lower DQE for a conventional single layer copper-Lanex® imager (where Lanex® is an x-ray conversion material commercially available from Kodak Corporation of Rochester, N.Y.). As with the embodiment described with respect to FIG. 3 above, this lower DQE value for the conventional single layer imager results in low contrast images of the tumorous tissue making targeting of the tumor problematic, and can result in too high a dose being delivered to the patient.

Figure 7:
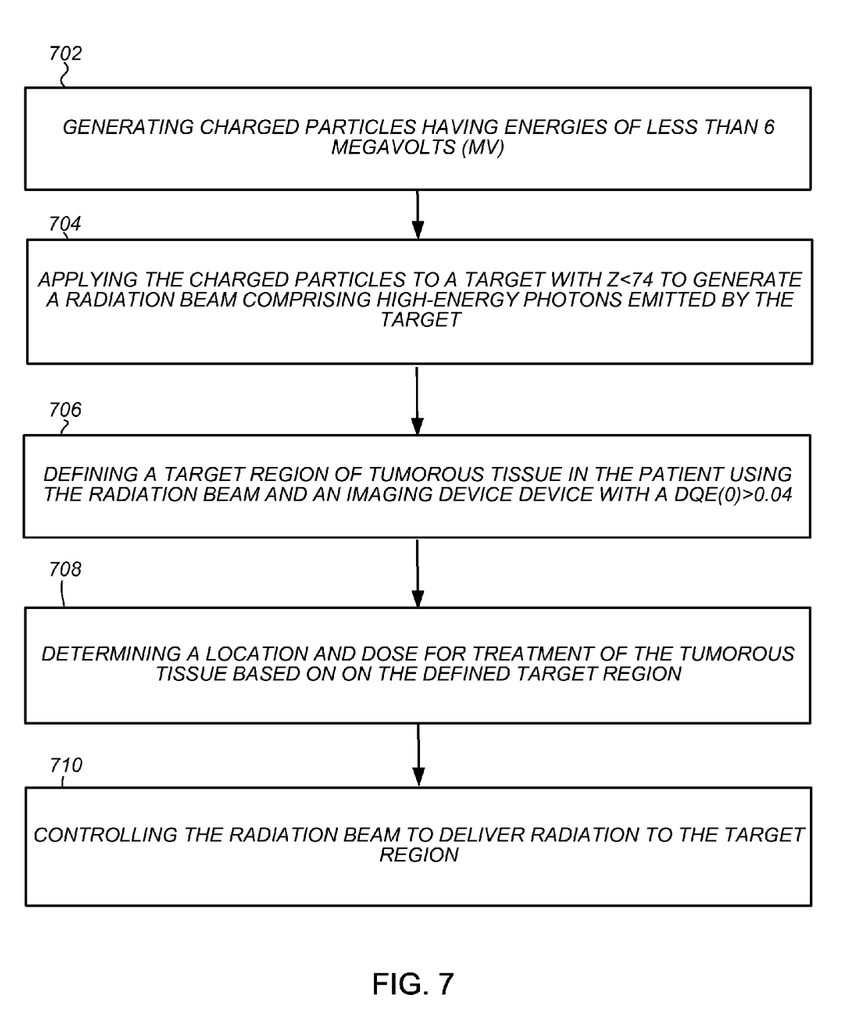
FIG. 7 is a flow diagram illustrating a method of operating a MV system according to an embodiment of the present invention to generate high contrast images.

FIG. 7 is a flow diagram illustrating one embodiment of a method for operating an MV system according to an embodiment of the present invention to treat a patient with radiation. The method begins with generating charged particles having energies of less than about 6 MV (step 702). As noted above, in some embodiments the charged particles have energies ranging from about 2.5 to about 5.5 MV. Next, the charged particles are applied to an x-ray target 208 to generate a radiation beam comprising high-energy photons emitted by the x-ray target 208 (step 704). Generally, the x-ray target 208 includes a material having an atomic number (Z) of less than about 74, and is selected to emit high-energy x-ray photons. In certain preferred embodiments the x-ray target 208 substantially does not include Tungsten, but includes Aluminum (Z=13) and/or Beryllium (Z=4) and/or Carbon (Z=12). A target region of tumorous tissue in the patient is defined using the radiation beam and an imaging device 220 (step 706), and a location and dose for treatment of the tumorous tissue determined based on the defined target region (step 708). Generally, the imaging device 220 includes a flat panel imager having high detective quantum efficiency (DQE). In some embodiments the imaging device 220 is an imager 500 including a plurality of alternating scintillator layers 502 and photo-detector layers 504. Finally, the radiation beam is controlled to deliver radiation to substantially just the target region. (step 710). As described above, the radiation beam is controlled by a controller 214 that operates a collimator 210, which determines the shape of the radiation beam, and a linear accelerator 204 that generates the radiation beam. Optionally, the controller can further receive a current or voltage signal from the imaging device to pulse-width-modulate radiation dose delivered to the target region using the collimator.

Thus, embodiments of MV systems and methods for imaging and treatment of tumorous tissue in a patient have been described. In particular it is noted that the system and method of the present invention provides better image contrast while still maintaining enough MV photons for good treatment delivery combines a reduction in MV energy of the treatment beam (e.g. less than about 6 MV), a lowering of the atomic number (Z) of a target material from that of the typically used tungsten (Z=74) to a material with a Z of 13 or less, with the use of a high DQE imager (DQE(0)>0.04) to provide better image contrast while still maintaining sufficient MV photons for good treatment delivery.

Although the present disclosure has been described with reference to specific exemplary embodiments, it will be evident that various modifications and changes may be made to these embodiments without departing from the broader spirit and scope of the disclosure. Accordingly, the specification and drawings are to be regarded in an illustrative rather than a restrictive sense.

The Abstract of the Disclosure is provided to comply with 37 C.F.R. §1.72(b), requiring an abstract that will allow the reader to quickly ascertain the nature of one or more embodiments of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

Reference in the description to one embodiment or an embodiment means that a particular feature, structure, or characteristic described in connection with the embodiment is included in at least one embodiment of the circuit or method. The appearances of the phrase one embodiment in various places in the specification do not necessarily all refer to the same embodiment.

What is claimed is:

1. A system comprising:
    a radiation source for generating a radiation beam comprising high-energy photons for both imaging and treatment of tumorous tissue in a patient, the radiation source including a charged particle accelerator that generates charged particles having energies of less than 6 megavolts (MV), a low Z target to receive the charged particles and generate the high-energy photons of preferred lower energy content distributions in the radiation beam, and a collimator to shape the radiation beam;
    an imaging device with a high detective quantum efficiency (DQE (0)>0.04) to define a shape and a distribution of a beam illuminated target region of the tumorous tissue in the patient; and
    a controller to determine a location and modulate a dose for treatment of the tumorous tissue based on the imaging device defined target region and to control the collimator to establish a shape and an intensity distribution of the radiation beam delivered to the target region.

2. The system of claim 1, wherein the charged particles having energies ranging from 2.5 to 5.5 MV.

3. The system of claim 2, wherein the high-energy photons comprise x-rays.

4. The system of claim 3, wherein the target comprises a material having an atomic number (Z) of less than 74.

5. The system of claim 4, wherein the target substantially does not include tungsten.

6. The system of claim 5, wherein the target comprises aluminum.

7. The system of claim 5, wherein the target comprises beryllium.

8. The system of claim 5, wherein the target comprises carbon.

9. The system of claim 1, wherein the imaging device comprises a flat panel imager including a plurality of alternating scintillator layers and photo-detector layers.

* * * * *